(12) United States Patent
Finkeldei et al.

(10) Patent No.: US 8,624,066 B2
(45) Date of Patent: Jan. 7, 2014

(54) PROCESS FOR PREPARING METHYLMERCAPTOPROPIONALDEHYDE

(75) Inventors: Caspar Heinrich Finkeldei, Alzenau (DE); Pablo Zacchi, Bruchkoebel (DE); Benjamin Fonfe, Frankfurt (DE); Stephan Kretz, Biebergemuend (DE); Martin Koerfer, Kahl (DE); Hans Joachim Hasselbach, Gelnhausen (DE); Wolfgang Boeck, Langenselbold (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/337,434

(22) Filed: Dec. 27, 2011

(65) Prior Publication Data
US 2012/0165573 A1 Jun. 28, 2012

Related U.S. Application Data

(60) Provisional application No. 61/499,912, filed on Jun. 22, 2011.

(30) Foreign Application Priority Data

Dec. 28, 2010 (DE) .......................... 10 2010 064 250

(51) Int. Cl.
*C07C 319/18* (2006.01)

(52) U.S. Cl.
USPC .......................................................... 568/41

(58) Field of Classification Search
USPC .......................................................... 568/41
See application file for complete search history.

(56) References Cited

U.S. PATENT DOCUMENTS

| 2,626,282 | A |   | 1/1953 | Cunningham et al. |
| 4,225,516 | A |   | 9/1980 | Biola et al. |
| 5,637,766 | A | * | 6/1997 | Hsu et al. ....................... 562/512 |
| 6,057,481 | A | * | 5/2000 | Brockwell et al. .............. 568/41 |

FOREIGN PATENT DOCUMENTS

DE 26 27 430 A1 12/1976

OTHER PUBLICATIONS

International Search Report issued May 18, 2012 in PCT /EP2011/ 072868 (with English translation of Category of Cited Documents).

* cited by examiner

*Primary Examiner* — Sikarl Witherspoon
(74) *Attorney, Agent, or Firm* — Oblon, Spivak, McClelland, Maier & Neustadt, L.L.P.

(57) ABSTRACT

A process for preparing methylmercaptopropionaldehyde in a single reaction unit, is provided. According to the preferred embodiment, the process comprises, simultaneously contacting a gaseous mixture comprising acrolein with a liquid mixture comprising methylmercaptopropionaldehyde, methyl mercaptan, a catalyst and methylmercaptopropionaldehyde methyl thiohemiacetal in the reactive absorber; absorbing the acrolein from the gaseous mixture into the liquid mixture; reacting the absorbed acrolein with the methyl mercaptan or the methylmercaptopropionaldehyde methyl thiohemiacetal to obtain methylmercapto-propionaldehyde; removing gaseous impurities and by-products from the liquid mixture; and separating the obtained methylmercaptopropionaldehyde product from the reactive absorber, directing a portion of the separated product to storage or further processing and recycling the remaining portion to the reactive absorber; wherein the methyl mercaptan optionally comprises dimethyl sulfide or dimethyl ether.

20 Claims, 1 Drawing Sheet

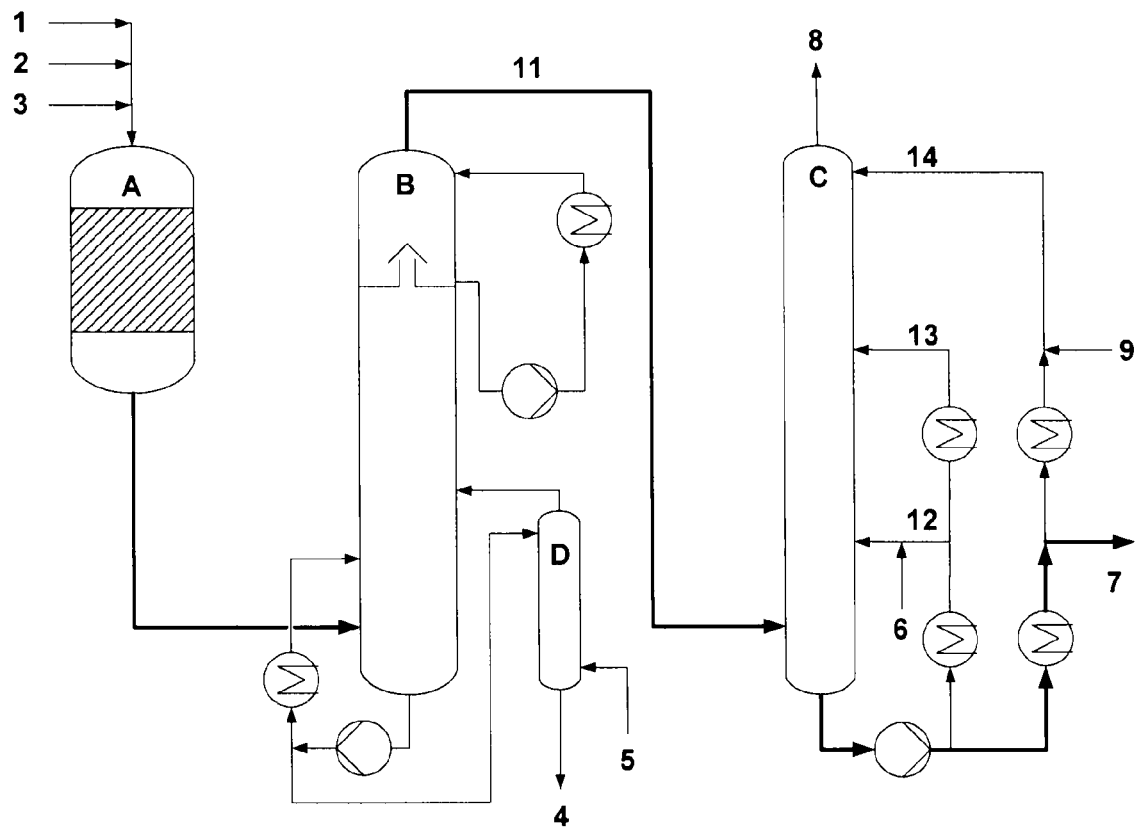
Flow diagram

PROCESS FOR PREPARING METHYLMERCAPTOPROPIONALDEHYDE

CROSS REFERENCE TO RELATED APPLICATIONS

This application claims priority to German Application No. 102010064250.9 filed Dec. 28, 2010 and to U.S. Provisional Application No. 61/499,912, filed Jun. 22, 2011, the disclosures of which are incorporated herein by reference in their entireties.

BACKGROUND OF THE INVENTION

The invention provides a process for preparing methylmercaptopropionaldehyde (MMP) from gaseous acrolein (AC) and methyl mercaptan (MC). The present invention provides, more particularly, a process for preparing methylmercaptopropionaldehyde from gaseous acrolein and methyl mercaptan, in one process step, wherein simultaneously, (a) gaseous acrolein is absorbed to a mixture comprising at least one compound from the group consisting of the methylthio hemiacetal of methylmercaptopropionaldehyde, methylmercaptopropionaldehyde and methyl mercaptan, (b) in this mixture, acrolein is reacted with methyl mercaptan and/or the hemithioacetal of methylmercaptopropionaldehyde to give methylmercaptopropionaldehyde and (c) impurities and by-products are removed from this mixture.

MMP formation from methyl mercaptan and a gas mixture comprising acrolein is conventionally known.

DE 2627430 describes a two-stage process wherein, in the first stage, the AC is absorbed from a gas mixture in MMP and, in a second stage, the AC dissolved in MMP reacts with MC at temperatures between 10 and 50° C. in the presence of a catalyst. A great economic disadvantage of this separation in two stages is the necessity of MMP recycling at −10° C. in order to completely absorb AC in MMP. The MMP yield based on the MMP introduced into the absorption column in the example described is 99%. At the same time, preferably 0.1 to 0.2% hemithioacetal is established in the reaction mixture. At hemithioacetal concentrations below 0.1%, AC is lost due to incomplete conversion, whereas at hemithioacetal concentrations above 1% the yield of the MMP reaction worsens. The gas mixture formed during the catalytic oxidation of propylene is absorbed from the acrylic acid present in a solvent such as, for example, tri-n-butyl phosphate (FR 7718136), a mixture of biphenyl and diphenyl ether (FR 1393175) or water (FR 1393175), and, after performance of this process step, freed of water in a condenser at −5-0° C. This condensation step too leads to higher capital and operating costs.

According to NL-A 68/09647, it may also be possible to first contact MC with MMP in the reaction zone and to contact the mixture thus obtained with the AC-containing gas. However, an additional step is needed here for treatment of the aqueous phase (extraction), and only an MMP yield of 91% based on the AC used is achieved.

WO 9429254 describes the continuous preparation of MMP from an acrolein-containing gas mixture and MC in a "gas/liquid" reaction zone, in which uncondensable gases are additionally separated from the AC process. Hemithioacetal formation is prevented by the equimolar addition of MC and AC, monitored preferably by periodic use of gas chromatography. According to the description, it may be possible to increase the MMP formation rate by a factor of 3-10. The limitation of the AC mass transfer is minimized by turbulent conditions in the reaction system.

In all documents described above, MC worked up by distillation is used. This is evident from the fact that the principle secondary components from the MC reaction, such as dimethyl sulphide and dimethyl disulphide, are present neither in the MMP product nor in the MMP offgas (WO 9429254 and U.S. Pat. No. 4,319,047). MC is usually synthesized in the gas phase at temperatures between 300 and 500° C. and at pressures between 1 and 25 bar. One process is described, for example, in EP 850922. The product mixture of the synthesis comprises, as well as the desired MC, the water formed in the reaction and, as by-products, dimethyl sulphide, dimethyl ether, small amounts of polysulphides, and unconverted methanol, excess hydrogen sulphide, and the gases which are inert for the purposes of the reaction: nitrogen, carbon monoxide, carbon dioxide and hydrogen. The separation of the product gas mixture into its components serves for recovery of methyl mercaptan and dimethyl sulphide, for discharge of water and inert gas components, and for recycling of unconsumed methanol and hydrogen sulphide into the synthesis reactor. This gives rise, for example, to pure MC with an MC content of up to 99.6% by weight (EP 0850923 and DE 1768826). Disadvantages of this distillative workup of the complex reaction mixture are, in addition to the high capital and operating costs, the unavoidable formation of residues which require disposal and the associated loss of materials of value.

DE 10359636 describes a process which avoids the high distillation complexity to obtain pure methyl mercaptan and nevertheless uses the methyl mercaptan obtained in the catalytic reaction of $H_2S$ with methanol, without losses, for the further conversion to MMP with liquid AC. Based on the crude MC used, the isolated yield is virtually quantitative, i.e. >99.9%. This is achieved by distillative removal of the constituents from the MC synthesis still present in the MMP reaction mixture, and preferably by the supply of an inert entraining agent, for example nitrogen. This reference does not disclose the use of AC-containing gases.

U.S. Pat. No. 3,529,940 discloses that reaction temperatures in the MMP synthesis can be controlled by dividing the exothermicity of hemithioacetal formation as intermediate and, after subsequent addition of liquid AC, the MMP reaction enthalpy of the MMP reaction into 2 zones. However, the the use of AC-containing gases is not disclosed.

SUMMARY OF THE INVENTION

Accordingly, an object of the present invention, is to provide a method to prepare MMP of maximum purity and maximum yield in a minimum number of process steps, from AC-containing gas without separate water condensation and from crude MC (MC>87% by weight, dimethyl sulphide 1.5-5% by weight, dimethyl disulphide 0.2-1% by weight, dimethyl ether 0-3% by weight, water ~0-2% by weight and methanol ~0-2% by weight).

This and other objects are provided by the present invention, a first embodiment of which provides process for preparing methylmercaptopropionaldehyde in a single reaction unit, comprising, simultaneously:

contacting a gaseous mixture comprising acrolein with a liquid mixture comprising methylmercaptopropionaldehyde, methyl mercaptan, a catalyst and methylmercaptopropionaldehyde methyl thiohemiacetal in the reaction unit;

absorbing the acrolein from the gaseous mixture into the liquid mixture;

reacting the absorbed acrolein with the methyl mercaptan or the methylmercaptopropionaldehyde methyl thiohemiacetal to obtain methylmercaptopropionaldehyde;

removing gaseous impurities and by-products from the liquid mixture; and separating the obtained methylmercaptopropionaldehyde product from the reaction unit, directing a portion of the separated product to storage or further processing and recycling the remaining portion to the reaction unit;

wherein the methyl mercaptan optionally comprises dimethyl sulfide or dimethyl ether.

BRIEF DESCRIPTION OF THE DRAWINGS

FIG. 1 shows a process flow diagram according to one embodiment of the invention.

DETAILED DESCRIPTION OF THE INVENTION

In an especially preferred embodiment, the present invention provides a process for preparing methylmercaptopropionaldehyde in a single reaction unit, comprising, simultaneously, in a single reactive absorber unit:

contacting a gaseous mixture comprising acrolein with a liquid mixture comprising methylmercaptopropionaldehyde, methyl mercaptan, a catalyst and methylmercaptopropionaldehyde methyl thiohemiacetal in the reactive absorber;

absorbing the acrolein from the gaseous mixture into the liquid mixture;

reacting the absorbed acrolein with the methyl mercaptan or the methylmercaptopropionaldehyde methyl thiohemiacetal to obtain methylmercaptopropionaldehyde;

stripping gaseous impurities and by-products from the top of the reactive absorber; and separating the obtained methylmercaptopropionaldehyde product from the reactive absorber, directing a portion of the separated product to storage or further processing and recycling the remaining portion to the reactive absorber;

wherein the methyl mercaptan optionally comprises dimethyl sulfide or dimethyl ether.

In the reaction of acrolein with methyl mercaptan and/or hemithioacetal, it may be assumed that hemithioacetal does not react directly with acrolein but first decomposes to acrolein and methyl mercaptan (equilibrium) and the methyl mercaptan thus released then reacts with acrolein to give MMP.

According to the embodiment, in only one vessel or in only one stage, gaseous AC is absorbed into a mixture of principally MMP, MC and hemithioacetal, where the AC reacts directly or via the hemithioacetal intermediate with MC to give MMP, and low-boiling secondary components (including dimethyl sulphide, acetaldehyde, water and dimethyl disulphide) are stripped, with minimization of the offgas losses of reactants and target product.

In an advantageous embodiment, the impurities removed may comprise at least one compound from the group consisting of dimethyl sulphide, acetaldehyde, water, dimethyl disulphide, methanol, carbon dioxide, propane, propene, hydrogen sulphide and dimethyl ether.

According to an especially preferred embodiment of the invention a water content of the product MMP is less than 2.5% by weight and it is unnecessary to remove water from the product in order to achieve MMP yields based on the AC used close to 100%. In a preferred embodiment, water is not removed additionally from the methylmercaptopropionaldehyde obtained.

In the present invention, MMP is produced from the chemical reaction between AC and MC. The AC required for this reaction may be obtained through partial oxidation of propylene in a gas phase reaction in a shell-and-tube reactor. After leaving the reactor, the AC-containing gas is freed in the quench column of excess water, unwanted by-products, for example acetic acid, formaldehyde, allyl alcohol, and principally acrylic acid. A small proportion of acetaldehyde is also separated out at this point. In the subsequent step, AC is absorbed from the gas phase in a mixture of MMP and hemithioacetal and reacts in the same vessel with MC or hemithioacetal.

In a preferred embodiment, the MC required for the reaction is metered continuously, in liquid or gaseous form, into an MMP feed stream to the reactive absorber.

The present invention may be a considerable simplification with respect to the above-described prior art, since the reactive absorber additionally functions as a stripping column and thus, in addition to the low-boiling substances from the AC-containing gas, also removes low-boiling secondary components from the reaction between hydrogen sulphide and methanol, for example dimethyl sulphide. It may thus be ensured that MC with low purity (MC>87% by weight, dimethyl sulphide 1.5-5% by weight, dimethyl disulphide 0.2-1% by weight, dimethyl ether 0-3% by weight, water ~0-2% by weight and methanol ~0-2% by weight) may also be used and hence a complex purification, as described, for example, in EP 0850923 and DE 1768826, may not be necessary. In an embodiment of the invention, the methyl mercaptan may contain 1.5-5% by weight of dimethyl sulphide and 0-3% by weight of dimethyl ether.

The present invention is described in detail hereinafter by a flow diagram (FIG. 1).

According to the embodiment according to FIG. 1, Acrolein is prepared in a catalytic gas phase reaction in the shell-and-tube reactor (A). At the inlet of the reactor, propylene (1) is mixed with air (2) and an inert gas stream (3) composed of nitrogen and small amounts of carbon dioxide and water vapour. The dilution of the reaction gas may be necessary in order to avoid the risk of an explosive mixture and to minimize temperature peaks in the catalyst bed. The temperature of the gas mixture may be about 130-200° C.

In addition to acrolein and water, by-products such as principally acrylic acid, acetic acid, formaldehyde, acetaldehyde, carbon dioxide and carbon monoxide may also be formed in the shell-and-tube reactor (A). The reaction gas enters a lower region of quench column (B), in which the temperature of the gas mixture is cooled rapidly by intensive contact with water. A majority of the water vapour in the gas mixture may be condensed. In this region of the column, a large proportion of the by-products, principally acrylic acid and acetic acid, may likewise be retained and leaves the column (B) via the bottom. This liquid is circulated by means of a "pumparound" system and is thus used as the cooling medium to quench the AC reaction gas. On the way to the top of the column, the reaction gas is contacted in counterflow to a water stream, which brings about a further reduction in the by-product content in the reaction gas. This water stream forms from the condensation by further cooling of the reaction gas to <20° C. (1.2-2.5 bar) in the upper region of the column (B) (upper pumparound). The liquid stream leaving the column (B) can be pumped to the top of a stripping column (D) in which the majority of the dissolved acrolein can be recovered. The stripping medium (5) used may be inert gases. The remaining liquid (4) may finally be sent to a thermal incineration for disposal.

From the top of the quench column (B), the AC-rich gas (11) enters the reactive absorber (C). In a highly preferred embodiment the AC-rich gas enters the reactive absorber via a jet pump (not shown). This may have the advantage that polymerization of AC can be avoided, an optimal pressure regime in the reactive absorber (C) is more readily possible and the upstream AC process can be conducted at lower pressures. In an alternative embodiment, the AC can also be fed directly into the lower section of the reactive absorber.

In the reactive absorber (C), AC is first absorbed in a mixture of principally MMP, free MC, methylmercaptopropionaldehyde methyl thiohemiacetal and water (12, 13, 14) and then reacts with MC or hemithioacetal in the presence of a homogeneous catalyst to form further MMP. In contrast to the prior art, there is no need either to avoid hemithioacetal formation from MC and MMP (WO 9429254) nor for MC to be present completely in the form of the hemithioacetal before the reaction with AC (U.S. Pat. No. 3,529,940) in order to obtain quantitative MMP yields based on the AC used. It may be advantageous that the mixture forms the hemithioacetal of methylmercaptopropionaldehyde by addition of methyl mercaptan onto methylmercaptopropionaldehyde in a concentration between 0.1 and 10% by weight, preferably between 1 and 10% by weight.

In an advantageous embodiment, the ratio between MC and AC in the liquid phase of the reactive absorber may be adjusted with the aid of an inline near infrared (NIR) measurement (accuracy +/−0.0005 mol/mol). It is advantageous that the ratio between methyl mercaptan and acrolein in the mixture is adjusted to a value between 0.95 and 1.1 mol/mol, preferably between 1.00 and 1.01 mol/mol, more preferably between 1.004 and 1.009 mol/mol, and especially preferably to 1.005 mol/mol.

In a preferred embodiment, the input concentration of the gaseous acrolein (11) in the mixture may be detected with the aid of an inline Fourier transform infrared (FTIR) measurement in order to adjust the feed rate, i.e. in order to be able to adjust the MC metering (6) at a very early stage. These inline measurements have the advantage that it is possible to react immediately to changes in the system and hence to keep the offgas losses of reactant and product low and the MMP product quality continuously at a high level.

The MMP reaction proceeds principally on the internals and in the bottom of the column (C). The internals used may, for example, be structured packings, random packings or trays. The pressure at the top of the column (C) is in the range from 1 to 2.5 bar, preferably from 1.2 to 1.6 bar. A pump circulates a portion of the MMP from the column bottom through two heat exchangers connected in series in order to reduce the temperature of this stream. In the first stage, cooling is effected with "cooling tower water (CTW)" to ~35° C., and then with "chilled water (CW)" to 0-20° C., preferably 5-10° C. A large portion of the MMP thus cooled enters at the top of the reactive absorber (C) (14) and functions as absorption/reaction medium. A further portion of the MMP is removed either after the first (preferred) or the second cooling step as product stream (7). A second pumparound, which in the standard case uses MMP from the bottom of the column (C), enters as absorption/reaction medium (13) in the middle region of the column (C). The temperature of this stream is in the range of 20-50° C., preferably 30-40° C. A third pumparound (12) in a particularly preferred embodiment enters the column below (13). Liquid and/or gaseous MC (6) is preferably added to this stream, but can also be supplied at any other point, preferably in the lower region of the column, into one of the other pumparounds.

The temperatures in the lower part of the column can be controlled by the heat exchanger in stream (12). The temperature in this part of the column may be in the range of 20° C. to 90° C., preferably 40° C. to 75° C. The low temperatures at the top of column (C) help to minimize AC, MC and MMP losses. However, excessively low temperatures may cause the retention of unwanted components such as dimethyl sulphide (DMS) and acetaldehyde (AA). These components are by-products of the MC or AC reaction and have to be substantially removed before MMP can be used, for example, in methionine production or the production of other compounds based on MMP. In the standard case of the invention, these by-products are substantially stripped in the reactive absorber (C) and are present in the offgas (8) which leaves the column (C) at the top and is then supplied to a thermal incineration.

In an advantageous embodiment, the impurities and by-products are removed from the mixture by stripping at 0.3 to 5 bar, preferably at 1 to 2 bar, and at 5 to 70° C., preferably at 5 to 20° C.

In an advantageous embodiment, the process step may be performed in the presence of a homogeneous and/or heterogeneous catalyst (9). This catalyst is preferably dimethylbenzylamine (DMBA) and/or triethanolamine. It may be additionally advantageous that the concentration of the catalyst in the mixture is in the range from 50 to 500 ppmw, preferably in the range from 130 to 150 ppmw.

To regulate the pH and the associated better storage stability of the MMP produced, it may be advantageous to continuously supply to the mixture at least one compound from the group consisting of inorganic and organic acids, preferably acetic acid and tartaric acid, and inorganic and organic bases, preferably triethanolamine.

These substances may form, for example in a mixture with DMBA, a catalyst/stabilizer mixture which is supplied continuously to the reactive absorber (C). In principle, other acids and bases may also possible. EP 1408029 describes, by way of example, inorganic oxo acids, for example sulphuric and phosphoric acid, hydrogen halides, for example hydrogen fluoride, bromide and chloride. Also suitable are organic acids, for example aliphatic monocarboxylic acids (e.g. formic acid, propionic acid, octanoic acid, acrylic acid, trichloroacetic acid, trifluoroacetic acid), aliphatic polycarboxylic acids (oxalic acid, succinic acid, adipic acid), aromatic monocarboxylic acids (phenylacetic acid, benzoic acid, cinnamic acid, furoic acid, thiophenecarboxylic acid) and aromatic polycarboxylic acids (phthalic acid, monoesters of sulphuric acid, sulphonic acid).

Examples of basic substances are inorganic bases (ammonia, sodium hydroxide, potassium hydroxide, ammonium carbonate, sodium carbonate, potassium carbonate, sodium hydrogencarbonate, potassium hydrogencarbonate, ammonium acetate, sodium acetate, potassium acetate) and nitrogen-containing organic bases (piperidine, triethylamine, pyridine, quinoline, urotropin, N,N-dimethylaniline).

The present invention has the advantages that
    the absorption of AC from a gas, the MMP reaction using crude MC and the stripping of low boilers, for example DMS, DMDS, DME, methanol, $CO_2$, $H_2S$, water, propene, propane, acetaldehyde, is possible in one process step, in a reactive absorber,
    losses of MC, AC and MMP may be minimized,
    the MC/AC stoichiometry may be monitored by using an NIR and FTIR,
    a separate water condensation from the AC-containing gas may not be required, and
    the probability of polymer formation may be minimized.

Having generally described this invention, a further understanding can be obtained by reference to the following example which is intended to illustrate the advantageous aspects of the present invention and is not intended to be limiting.

1) Standard Case

The AC-containing gas stream (11) entering the reactive absorber (C) had the following composition (Table 1):

TABLE 1

Composition AC process gas (% by vol.)

| | |
|---|---|
| CO2 | 0.651 |
| O2 | 5.112 |
| Argon | 0.625 |
| N2 | 85.147 |
| H2O | 1.331 |
| Propene | 0.162 |
| Propane | 0.030 |
| CO | 0.354 |
| Acetaldehyde | 0.143 |
| Acrolein | 6.430 |
| Allyl alcohol | 0.003 |
| Allyl acrylate | 0.001 |
| Acetic acid | 0.011 |
| Acrylic acid | 0.000 |

In order to show the additional stripping effect on low boilers such as dimethyl sulphide and acetaldehyde, methyl mercaptan (6) in the composition below (Table 2) was introduced into the reactive absorber (C).

TABLE 2

MC composition (% by wt.)

| | |
|---|---|
| H2S | 0.212 |
| H2O | 0.860 |
| Dimethyl ether | 0.068 |
| Methanol | 0.410 |
| Methyl mercaptan | 95.981 |
| Dimethyl sulphide | 1.830 |
| Dimethyl disulphide | 0.650 |

For instance, the majority of dimethyl sulphide and acetaldehyde was present in the offgas (8), while only a very low proportion remained in the MMP product (7). The MC, AC and MMP losses were kept very low (Tables 3 and 4).

TABLE 3

MMP composition (% by wt.)

| | |
|---|---|
| Methyl mercaptan | 0.443 |
| Acetaldehyde | 0.043 |
| Dimethyl sulphide | 0.043 |
| Acrolein | 0.015 |
| Methanol | 0.126 |
| H2O | 2.415 |
| Dimethyl disulphide | 0.212 |
| Allyl alcohol | 0.025 |
| Allyl acrylate | 0.015 |
| Dimethylbenzylamine | 0.016 |
| MMP | 96.500 |
| Acrylic acid | 0.000 |
| Acetic acid | 0.148 |
| Dimethyl ether | 0.000 |

TABLE 4

Offgas composition (% by wt.)

| | |
|---|---|
| CO2 | 1.064 |
| H2S | 0.000 |
| Water | 0.341 |
| Propene | 0.254 |
| Propane | 0.049 |
| Dimethyl ether | 0.034 |
| Methanol | 0.016 |
| Acetaldehyde | 0.223 |
| Methyl mercaptan | 0.356 |
| Acrolein | 0.000 |
| Dimethyl sulphide | 0.216 |
| Allyl alcohol | 0.000 |
| Acetic acid | 0.014 |
| Dimethyl disulphide | 0.021 |
| Allyl acrylate | 0.000 |
| MMP | 0.150 |
| O2 | 6.079 |
| CO | 0.368 |
| N2 | 89.891 |
| Argon | 0.926 |

MMP product (7) was additionally distilled at 200° C. and at 30 mbar for 25 minutes in order to determine the residue concentration. Surprisingly, at 0.20-0.25% by weight, it was actually below the residue concentration of 0.30-0.40% by weight of an MMP sample which originated from an MMP process using liquid AC (U.S. Pat. No. 3,529,940). The evolution of the residue in the course of storage for up to 32 days in the present invention, at 0.03% by weight per day, was also lower than in a process using liquid AC (0.05% by weight per day).

In order to ensure the MMP quality for a downstream methionine process, no separate water condensation from the AC-containing gas (11), as described in DE 2627430, is thus necessary. A certain water content may even have a positive influence on the MMP formation rate since water has a higher degree of dissociation of the basic amine catalyst used up to a certain concentration. All by-product components in the MMP (7) was also within the specification for the downstream methionine process in spite of the use of the above-described crude MC (6). The sufficient stripping effect of the reactive absorber (C) was thus confirmed. The MC, AC and MMP losses in the offgas (8) were sufficiently low to be able to run the process economically. For very exact establishment of the MC/AC stoichiometry of 1.004-1.009, an NIR measuring unit in particular was suitable. Inline measurements allow a rapid reaction to a change in the process, for example an adjustment of the feed streams (AC and/or MC), and hence a constant MMP quality. In addition, reactant and product losses via the offgas (8) may thus be minimized. The input concentration of the AC gas may be effected via an online GC measurement, or else preferably via an inline FTIR measurement.

2) Influence of the MC Feed Point in the Reactive Absorber (C)

In the case of feeding of MC directly into the column (C), a great influence on the reaction system was discernible. The increased amount of MC which has to be absorbed in the column as a result, in conjunction with exothermic hemithioacetal formation, resulted in a distinct increase in the temperature profile in the reactive absorber (C). This effect led additionally to increased MC and AC losses in the offgas (8) (Table 5).

TABLE 5

Offgas losses (8) with different MC feed points

| Offgas (8) - Top [% by vol.] | Standard | MC metering directly into column |
|---|---|---|
| MC | 0.111 | 0.608 |
| AC | 0.030 | 0.281 |
| MMP | 0.040 | 0.057 |

The invention claimed is:

1. A process for preparing methylmercaptopropionaldehyde in a single reaction unit, comprising, simultaneously:
   contacting a gaseous mixture comprising acrolein with a liquid mixture comprising methylmercaptopropionaldehyde, methyl mercaptan, a catalyst and methylmercaptopropionaldehyde methyl thiohemiacetal in the reaction unit;
   absorbing the acrolein from the gaseous mixture into the liquid mixture;
   reacting the absorbed acrolein with the methyl mercaptan or the methylmercaptopropionaldehyde methyl thiohemiacetal to obtain methylmercaptopropionaldehyde;
   removing gaseous impurities and by-products from the liquid mixture; and
   separating the obtained methylmercaptopropionaldehyde product from the reaction unit, directing a portion of the separated product to storage or further processing and recycling the remaining portion to the reaction unit;
   wherein the methyl mercaptan optionally comprises dimethyl sulfide or dimethyl ether; and
   wherein a concentration of the methylmercaptopropionaldehyde methyl thiohemiacetal in the liquid mixture is from 1 to 10% by weight.

2. The process according to claim 1, wherein the gaseous impurities and by-products are removed from the reactive absorber by stripping at a temperature of 5 to 70 °C. and pressure of 0.3 to 5 bar.

3. The process according to claim 1, wherein the gaseous impurities and by-products comprise at least one compound selected from the group consisting of dimethyl sulfide, acetaldehyde, water, dimethyl disulphide, methanol, carbon dioxide, propane, propene, hydrogen sulfide and dimethyl ether.

4. The process according to claim 1, wherein the methyl mercaptan is supplied to the reaction unit continuously as a liquid, a gas or a mixture of liquid and gas.

5. The process according to claim 1, wherein the catalyst is a homogeneous catalyst, a heterogeneous catalyst or a combination thereof.

6. The process according to claim 1, wherein the catalyst is at least one of dimethylbenzylamine and triethanolamine.

7. The process according to claim 1, wherein a concentration of the catalyst in the liquid mixture is from 50 to 500 ppmw.

8. The process according to claim 1, further comprising:
   adjusting a mol ratio of methyl mercaptan to acrolein in the liquid mixture to a value between 0.95 and 1.1 mol/mol.

9. The process according to claim 8, the adjustment of the ratio of methyl mercaptan to acrolein in the liquid mixture comprises an inline determination of the ratio via near infrared (NIR) measurement.

10. The process according to claim 1, further comprising:
    adjusting a feed rate of the gaseous acrolein to the reaction unit by a method comprising determination of an acrolein concentration in the gaseous mixture with inline Fourier transform infrared (FTIR) measurement.

11. The process according to claim 1, further comprising continuously adding at least one compound from the group consisting of inorganic and organic acids to the liquid mixture.

12. The process according to claim 1, wherein the methyl mercaptan comprises 1.5-5% by weight of dimethyl sulphide and 0-3% by weight of dimethyl ether.

13. The process according to claim 1, wherein a water content of the product methylmercaptopropionaldehyde is less than 2.5% by weight.

14. The process according to claim 8, wherein a mol ratio of methyl mercaptan to acrolein in the liquid mixture is between 1.004 and 1.009 mol/mol.

15. The process according to claim 1, wherein a residue concentration of the methylmercaptopropionaldehyde is 0.25% by weight or less.

16. The process according to claim 11 wherein an inorganic acid is added to the reaction unit and the inorganic acid is at least one selected from the group consisting of sulfuric acid, phosphoric acid, hydrogen fluoride, hydrogen chloride and hydrogen bromide.

17. The process according to claim 11 wherein an organic acid is added to the reaction unit and the organic acid is at least one selected from the group consisting of acetic acid, formic acid, propionic acid, octanoic acid, acrylic acid, tartaric acid, trichloroacetic acid, trifluoroacetic acid, oxalic acid, succinic acid, adipic acid, phenylacetic acid, benzoic acid, cinnamic acid, furoic acid, thiophenecarboxylic acid and phthalic acid.

18. The process according to claim 1, further comprising continuously adding at least one compound from the group consisting of inorganic and organic bases to the liquid mixture.

19. The process according to claim 18, wherein an organic base is added to the reaction unit and the organic base is selected from the group consisting of triethanolamine, piperidine, triethylamine, pyridine, quinoline, urotropin and N,N-dimethylaniline.

20. The process according to claim 1, wherein the single reaction unit is a reactive a reactive absorber.

* * * * *

UNITED STATES PATENT AND TRADEMARK OFFICE
CERTIFICATE OF CORRECTION

| | | |
|---|---|---|
| PATENT NO. | : 8,624,066 B2 | Page 1 of 1 |
| APPLICATION NO. | : 13/337434 | |
| DATED | : January 7, 2014 | |
| INVENTOR(S) | : Caspar Heinrich Finkeldei et al. | |

It is certified that error appears in the above-identified patent and that said Letters Patent is hereby corrected as shown below:

On the Title Page, Item (57) ABSTRACT, line 11, "methylmercapto-propionaldehyde;" should read --methylmercaptopropionaldehyde;--.

In the Specification

Column 1, line 34, "50°C." should read --50°C--;

line 36, "-10°C." should read -- -10°C--.

Column 2, line 7, "500°C." should read --500°C--.

Column 4, line 56, "<20°C." should read --<20°C--.

Column 5, line 46, "~35°C." should read --~35°C--;

line 47, "0-20°C.," should read --0-20°C,--;

line 56, "20-50°C.," should read --20-50°C,--;

line 64, "20°C. to" should read --20°C to--; and line 65, "90°C., preferably 40°C." should read --90°C, preferably 40°C--.

Column 6, line 12, "70°C.," should read --70°C,--.

Column 8, line 17, "200°C." should read --200°C--.

In the Claims

Column 9, line 28, "70°C." should read --70°C--.

Column 10, line 46, "a reactive a reactive" should read --a reactive--.

Signed and Sealed this
Fifteenth Day of July, 2014

Michelle K. Lee
*Deputy Director of the United States Patent and Trademark Office*